United States Patent
Jerstroem et al.

(10) Patent No.: US 11,475,451 B2
(45) Date of Patent: Oct. 18, 2022

(54) BIOMETRIC AUTHENTICATION FOR, AND SECURE ELECTRONIC TRACKING OF, RESTRICTED OVER-THE-COUNTER DRUG SALES

(71) Applicant: Bayer Healthcare LLC, Whippany, NJ (US)

(72) Inventors: Goeran M. Jerstroem, Glen Ridge, NJ (US); Michael DeBiasi, Basking Ridge, NJ (US); Felix Sebastian Kaechele, Leverkusen (DE)

(73) Assignee: Bayer Healthcare LLC, Whippany, NJ (US)

( * ) Notice: Subject to any disclaimer, the term of this patent is extended or adjusted under 35 U.S.C. 154(b) by 0 days.

(21) Appl. No.: 15/937,358

(22) Filed: Mar. 27, 2018

(65) Prior Publication Data
US 2018/0285880 A1 Oct. 4, 2018

Related U.S. Application Data

(60) Provisional application No. 62/479,959, filed on Mar. 31, 2017.

(51) Int. Cl.
*G06Q 20/40* (2012.01)
*G06Q 20/32* (2012.01)
(Continued)

(52) U.S. Cl.
CPC ....... *G06Q 20/40145* (2013.01); *G06Q 20/20* (2013.01); *G06Q 20/202* (2013.01);
(Continued)

(58) Field of Classification Search
None
See application file for complete search history.

(56) References Cited

U.S. PATENT DOCUMENTS

| 7,006,893 B2 | 2/2006 | Hart et al. |
| 8,099,301 B2 | 1/2012 | Keresman, III et al. |

(Continued)

FOREIGN PATENT DOCUMENTS

| WO | 2004036479 | 4/2004 |
| WO | 2007044500 | 4/2007 |

(Continued)

OTHER PUBLICATIONS

Reducing Counterfeit Drugs with Blockchains: A Survey (Year: 2021).*
(Continued)

*Primary Examiner* — Bruce I Ebersman
(74) *Attorney, Agent, or Firm* — Morrison & Foerster LLP (57) ABSTRACT

A mobile device is provided that includes biometric sensor (s), and a processor that causes the biometric sensor(s) to acquire a physiological marker of a user, and identify and authenticate the user. The processor sends a message to an authentication server that indicates the user is authenticated, and receives a response from the authentication server that includes a unique authentication code. The processor receives selection of a thereby selected over-the-counter (OTC) drug, and communicates with a point-of-sale (POS) system with contactless payment capability. The processor sends a purchase message to the POS system that includes the unique authentication code, an identifier of the selected OTC drug, and payment information. And the POS system communicates with the authentication server to validate the unique authentication code, and with an authorization server to authorize payment for the selected OTC drug based on the payment information.

9 Claims, 10 Drawing Sheets

(51) Int. Cl.
*G16H 40/63* (2018.01)
*G07F 7/10* (2006.01)
*G07F 17/00* (2006.01)
*G06Q 20/20* (2012.01)
*G16H 20/10* (2018.01)

(52) U.S. Cl.
CPC ......... *G06Q 20/206* (2013.01); *G06Q 20/327* (2013.01); *G06Q 20/3278* (2013.01); *G06Q 20/405* (2013.01); *G07F 7/10* (2013.01); *G07F 17/0092* (2013.01); *G16H 20/10* (2018.01); *G16H 40/63* (2018.01); *G06Q 2220/00* (2013.01)

(56) References Cited

U.S. PATENT DOCUMENTS

| | | | |
|---|---|---|---|
| 8,344,847 B2 | 1/2013 | Moberg et al. | |
| 8,922,330 B2 | 12/2014 | Moberg et al. | |
| 9,517,304 B2 | 12/2016 | Moberg et al. | |
| 9,579,454 B2 | 2/2017 | Moberg et al. | |
| 10,091,180 B1* | 10/2018 | Moritz | G06F 21/602 |
| 10,171,476 B2* | 1/2019 | Khan | H04L 9/3234 |
| 10,971,251 B1* | 4/2021 | Giobbi | G06Q 10/10 |
| 2001/0047281 A1 | 11/2001 | Keresman, III et al. | |
| 2008/0086326 A1 | 4/2008 | Moura et al. | |
| 2008/0269947 A1* | 10/2008 | Beane | G06Q 20/40 700/241 |
| 2009/0138366 A1 | 5/2009 | Bemmel et al. | |
| 2010/0145861 A1* | 6/2010 | Law | G06Q 30/0601 705/40 |
| 2011/0006880 A1 | 1/2011 | Long et al. | |
| 2011/0009724 A1 | 1/2011 | Hill et al. | |
| 2011/0009725 A1 | 1/2011 | Hill et al. | |
| 2011/0009813 A1 | 1/2011 | Rankers | |
| 2011/0010257 A1 | 1/2011 | Hill et al. | |
| 2012/0101630 A1 | 4/2012 | Daya et al. | |
| 2012/0130747 A1 | 5/2012 | Keresman, III et al. | |
| 2013/0317645 A1 | 11/2013 | Daya et al. | |
| 2014/0263423 A1 | 9/2014 | Akdogan et al. | |
| 2014/0267719 A1 | 9/2014 | Akdogan et al. | |
| 2014/0277710 A1 | 9/2014 | Akdogan et al. | |
| 2014/0278508 A1 | 9/2014 | Akdogan et al. | |
| 2015/0134107 A1 | 5/2015 | Hyde et al. | |
| 2015/0134345 A1 | 5/2015 | Hyde et al. | |
| 2015/0134346 A1 | 5/2015 | Hyde et al. | |
| 2015/0144653 A1* | 5/2015 | Kline | G07F 9/001 222/23 |
| 2015/0223890 A1 | 8/2015 | Miller et al. | |
| 2015/0223891 A1 | 8/2015 | Miller et al. | |
| 2016/0117471 A1 | 4/2016 | Belt et al. | |
| 2016/0292668 A9* | 10/2016 | Laracey | G06Q 30/0241 |
| 2017/0119966 A1 | 5/2017 | Moberg et al. | |
| 2017/0161439 A1* | 6/2017 | Raduchel | G06F 21/31 |
| 2017/0173262 A1* | 6/2017 | Veltz | G16H 20/17 |
| 2017/0220762 A1 | 8/2017 | Toupin et al. | |
| 2017/0228692 A1 | 8/2017 | Pargoe | |
| 2017/0316408 A1* | 11/2017 | Bernesby | G06Q 20/3829 |
| 2018/0174097 A1* | 6/2018 | Liu | H04L 9/3239 |
| 2018/0285879 A1* | 10/2018 | Gadnis | G06Q 20/3223 |
| 2019/0108709 A1* | 4/2019 | Yamazaki | G07F 13/065 |
| 2021/0045640 A1* | 2/2021 | Poltorak | A61B 5/6847 |

FOREIGN PATENT DOCUMENTS

| | | |
|---|---|---|
| WO | 2011005633 | 1/2011 |
| WO | 2012109229 | 8/2012 |
| WO | 2015073375 | 5/2015 |
| WO | 2015120000 | 8/2015 |
| WO | 2015120002 | 8/2015 |
| WO | 2017027673 | 2/2017 |
| WO | 2017099825 | 6/2017 |

OTHER PUBLICATIONS

Blockchain & IoT based Drugs Traceability for Pharma Industry (Year: 2021).*

Jedhe, Arjun, "Biometric Storage and Retrieval of the Emergency Medical Records", The Patent Act 1970 and The Patents Rules, 2003, Feb. 2017, pp. 1-12.

Lee, Justin, "Facial recognition for online stores: Q&A with Hoyos Labs CEO Hector Hoyos", BiometricUpdate.com, Nov. 2015, Retrieved from http://www.biometricupdate.com/201511/facial-recognition-for-online-stores-qa-with-hoyos-labs-ceo-hector-hoyos.

International Search Report dated Jun. 28, 2018 in corresponding international application No. PCT/IB2018/052102 filed Mar. 27, 2018.

* cited by examiner

BIOMETRIC AUTHENTICATION FOR, AND SECURE ELECTRONIC TRACKING OF, RESTRICTED OVER-THE-COUNTER DRUG SALES

CROSS-REFERENCE TO RELATED APPLICATION(S)

The present application claims priority to U.S. Provisional Patent Application No. 62/479,959, entitled: Biometric Authentication for, and Secure Electronic Tracking of Restricted Over-the-Counter Drug Sales, filed on Mar. 31, 2017, the content of which is incorporated herein by reference in its entirety.

TECHNOLOGICAL FIELD

The present disclosure relates generally to biometric authentication and contactless payment systems and, in particular, to biometric authentication for, and secure electronic tracking of, restricted over-the-counter drug sales.

BACKGROUND

Biometric authentication involves use of physiological markers to identify and thereby authenticate. These physiological markers include, for example, fingerprint, palm print, hand geometry, face recognition, iris recognition, retina recognition and the like. The technology is becoming more commonplace in a number of applications including contactless payment systems in which smartphones and other mobile devices use short-range communication technology to make secure payments at the point of sale. Apple Pay, Android Pay and Samsung Pay are three systems that use fingerprint authentication.

While biometric authentication and contactless payment systems have made a number of point-of-sale transactions easier and more efficient, there are a number of transactions that remain complicated. One example of a complicated point-of-sale transaction is for the sale of certain restricted over-the-counter (OTC) (i.e., non-prescription) drugs such as those drugs covered by the Combat Methamphetamine Epidemic Act of 2005 (CMEA) in the United States. The CMEA regulates products contained in certain OTC drugs including ephedrine and pseudoephedrine (PSE) because of their use in the manufacture of illegal drugs. The CMEA requires merchants to restrict public access to regulated products, verify proof of identity of all purchasers (e.g., government-issued identification), and track all purchasers and purchases.

Therefore it would be desirable to have a system and method that takes into account at least some of the issues discussed above, as well as other possible issues.

BRIEF SUMMARY

In view of the foregoing background, example implementations of the present disclosure are directed to biometric authentication and contactless payment systems and, in particular, to biometric authentication for, and secure electronic tracking of, restricted over-the-counter drug (e.g., PSE) sales.

The present disclosure thus includes, without limitation, the following example implementations.

Some example implementations provide a mobile device comprising one or more biometric sensors configured to acquire a physiological marker from which a user is identifiable and thereby authenticated; a short-range communication interface configured to implement short-range communication technology and enable contactless payment capability of the mobile device; and a processor coupled to the one or more biometric sensors and short-range communication interface, and programmed to at least: cause the one or more biometric sensors to acquire the physiological marker, and identify and authenticate the user based thereon; send a message to an authentication server that indicates the user is authenticated, and receive a response from the authentication server that includes a unique authentication code; receive selection of a thereby selected over-the-counter (OTC) drug; and communicate with a point-of-sale (POS) system with contactless payment capability, to purchase the selected OTC drug using the short-range communication interface and the contactless payment capabilities of the mobile device and POS system, wherein the processor being programmed to communicate with the POS system includes being programmed to send a purchase message to the POS system that includes the unique authentication code, an identifier of the selected OTC drug, and payment information, the POS system being configured to communicate with the authentication server to validate the unique authentication code, and with an authorization server to authorize payment for the selected OTC drug based on the payment information.

In some example implementations of the mobile device of any preceding example implementation, or any combination of any preceding example implementations, the POS system has a known location, and the processor being programmed to authenticate the user based on the physiological marker and communicate with the POS system using the short-range communication interface locks-in the user thereby authenticated at the known location.

In some example implementations of the mobile device of any preceding example implementation, or any combination of any preceding example implementations, the authentication server is operated by a service provider, and the processor is further programmed to enable the service provider to verify an identity of the user, including the processor being programmed to at least capture data from a proof of identity of the user; and send the data to the service provider to enable the service provider to verify the identity of the user from the data, the identity of the user being verified before the authentication server is enabled to send the response that indicates the unique authentication code.

In some example implementations of the mobile device of any preceding example implementation, or any combination of any preceding example implementations, the processor is further programmed to enable the user to register an account with the service provider before the message is sent to the authentication server, and during which the processor is programmed to enable the service provider to verify the identity of the user.

Some example implementations provide apparatus configured to implement a self-service kiosk or integrated shelf dispenser, the apparatus comprising one or more biometric sensors configured to acquire a physiological marker from which a user is identifiable and thereby authenticated; and a processor coupled to the one or more biometric sensors, and programmed to at least: cause the one or more biometric sensors to acquire the physiological marker, and identify and authenticate the user based thereon; send a message to an authentication server that indicates the user is authenticated, and receive a response from the authentication server that includes a unique authentication code; receive selection of a thereby selected over-the-counter (OTC) drug; complete a purchase of the selected OTC drug, including the processor being programmed to send a purchase message to the authentication server that includes the unique authentication code, an identifier of the selected OTC drug, and payment information, the processor being programmed to send the purchase message for the authentication server to validate the unique authentication code, and for the authentication server to cooperate with an authorization server to authorize payment for the selected OTC drug based on the payment information; and receive an encrypted code to authorize release of the selected OTC drug; and a dispenser coupled to the processor and caused thereby to dispense the selected OTC drug after the purchase is completed.

In some example implementations of the apparatus of any preceding example implementation, or any combination of any preceding example implementations, the authentication server is operated by a service provider, and the processor is further programmed to enable the service provider to verify an identity of the user, including the processor being programmed to at least capture data from a proof of identity of the user; and send the data to the service provider to enable the service provider to verify the identity of the user from the data, the identity of the user being verified before the authentication server is enabled to send the response that indicates the unique authentication code.

In some example implementations of the apparatus of any preceding example implementation, or any combination of any preceding example implementations, the processor is further programmed to enable the user to register an account with the service provider before the message is sent to the authentication server, and during which the processor is programmed to enable the service provider to verify the identity of the user.

Some example implementations provide an apparatus configured to implement an authentication server, the apparatus comprising a processor and a memory storing executable instructions that in response to execution by the processor cause the apparatus to at least: receive a message related to a purchase of an over-the-counter (OTC) drug by a user, the message indicating the user is authenticated, the message being received from a mobile device, self-service kiosk or integrated shelf dispenser; send a response to the mobile device, self-service kiosk or integrated shelf dispenser, the response including a unique authentication code; receive a purchase message that includes the unique authentication code, an identifier of a selected OTC drug, and payment information, the purchase message being received from a point-of-sale (POS) system, or the self-service kiosk or integrated shelf dispenser; validate the unique authentication code; cooperate with an authorization server to authorize payment for the selected OTC drug based on the payment information; and return an encrypted code to the POS system, self-service kiosk or integrated shelf dispenser to authorize release of the selected OTC drug.

In some example implementations of the apparatus of any preceding example implementation, or any combination of any preceding example implementations, the memory stores executable instructions that in response to execution by the processor cause the apparatus to further at least electronically record a purchase transaction including the user, the selected OTC drug and a date or time of purchase of the selected OTC drug.

In some example implementations of the apparatus of any preceding example implementation, or any combination of any preceding example implementations, the purchase transaction identifies the user by the unique authentication code or a physiological marker of the user.

In some example implementations of the apparatus of any preceding example implementation, or any combination of any preceding example implementations, the apparatus being caused to electronically record the purchase transaction includes being caused to electronically record the purchase transaction on a blockchain.

In some example implementations of the apparatus of any preceding example implementation, or any combination of any preceding example implementations, the purchase transaction identifies the user by the unique authentication code or a physiological marker of the user, and identifies the selected OTC drug by an identifier of the selected OTC drug that is unique to a unit thereof, wherein the identifier of the selected OTC drug is recorded on the blockchain during manufacturing or packaging, and the apparatus is thereafter caused to electronically record the purchase transaction including the unique authentication code or physiological marker of the user, the identifier of the selected OTC drug, and the date or time of purchase.

Some example implementations provide a method comprising acquiring, via one or more biometric sensors of a mobile device, a physiological marker from which a user is identifiable and thereby authenticated; and at the mobile device; identifying and authenticating the user based on the physiological marker; sending a message to an authentication server that indicates the user is authenticated, and receiving a response from the authentication server that includes a unique authentication code; receiving selection of a thereby selected over-the-counter (OTC) drug; and communicating with a point-of-sale (POS) system with contactless payment capability, to purchase the selected OTC drug using the short-range communication interface and the contactless payment capabilities of the mobile device and POS system, wherein communicating with the POS system includes sending a purchase message to the POS system that includes the unique authentication code, an identifier of the selected OTC drug, and payment information, the POS system communicating with the authentication server to validate the unique authentication code, and with an authorization server to authorize payment for the selected OTC drug based on the payment information.

In some example implementations of the method of any preceding example implementation, or any combination of any preceding example implementations, the POS system has a known location, and authenticating the user based on the physiological marker and communicating with the POS system using the short-range communication interface locks-in the user thereby authenticated at the known location.

In some example implementations of the method of any preceding example implementation, or any combination of any preceding example implementations, the authentication server is operated by a service provider, and the method further comprises enabling the service provider to verify an identity of the user, including at least capturing data from a proof of identity of the user; and sending the data to the service provider to enable the service provider to verify the identity of the user from the data, the identity of the user being verified before the authentication server is enabled to send the response that indicates the unique authentication code.

In some example implementations of the method of any preceding example implementation, or any combination of any preceding example implementations, the method further comprises enabling the user to register an account with the service provider before the message is sent to the authentication server, and during which the service provider is enabled to verify the identity of the user.

Features, aspects, and advantages of the present disclosure will be apparent from a reading of the following detailed description together with the accompanying drawings, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as combinable, unless the context of the disclosure clearly dictates otherwise.

BRIEF DESCRIPTION OF THE DRAWING(S)

Having thus described the disclosure in general terms, reference will now be made to the accompanying drawings, which are not necessarily drawn to scale, and wherein:

DETAILED DESCRIPTION

Some implementations of the present disclosure will now be described more fully hereinafter with reference to the accompanying drawings, in which some, but not all implementations of the disclosure are shown. Indeed, various implementations of the disclosure may be embodied in many different forms and should not be construed as limited to the implementations set forth herein; rather, these example implementations are provided so that this disclosure will be thorough and complete, and will fully convey the scope of the disclosure to those skilled in the art. As used herein, for example, the singular forms "a," "an," "the" and the like include plural referents unless the context clearly dictates otherwise. The terms "data," "information," "content" and similar terms may be used interchangeably, according to some example implementations of the present invention, to refer to data capable of being transmitted, received, operated on, and/or stored. Also, for example, reference may be made herein to quantitative measures, values, relationships or the like. Unless otherwise stated, any one or more if not all of these may be absolute or approximate to account for acceptable variations that may occur, such as those due to engineering tolerances or the like. Like reference numerals refer to like elements throughout.

Figure 1:
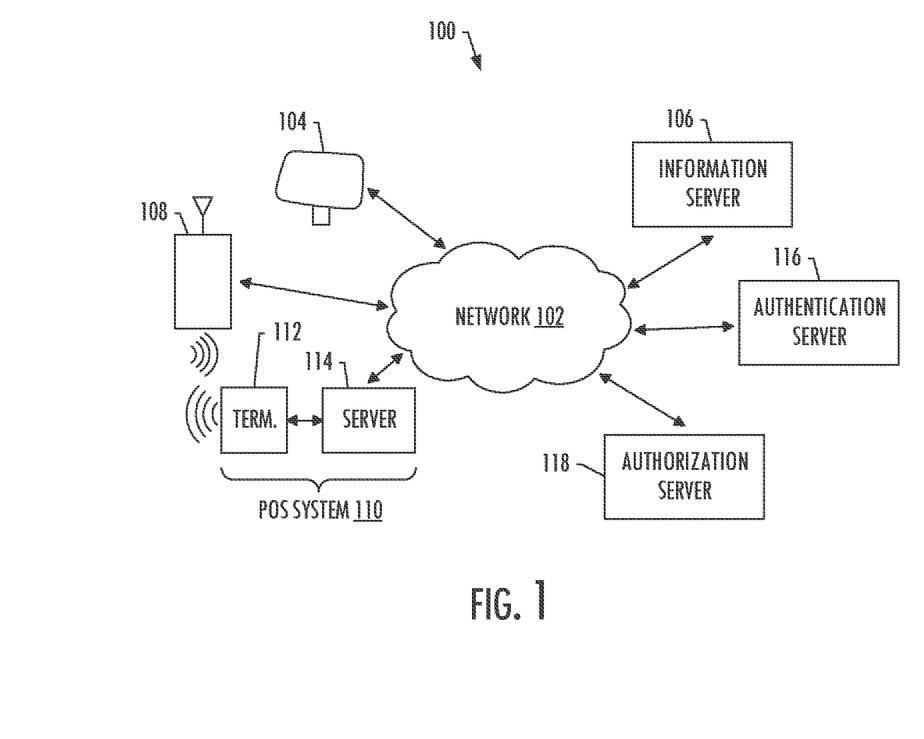
FIG. 1 illustrates a system 10 according to example implementations of the present disclosure.

FIG. 1 illustrates a system 100 according to example implementations of the present disclosure. As shown, the system may be implemented with an Internet-based computing architecture including a computer network or a number of interconnected computer networks 102 in or over which a number of systems, computers and the like communicate or otherwise operate. As shown, these include a dynamic display 104, an information server 106, a mobile device 108, a point-of-sale (POS) system 110 including a POS terminal 112 and server 114, and authentication 116 and authorization 118 server computers. Although shown and described herein in the context of an Internet-based computing architecture, it should be understood that the system may implemented with any of a number of different network-based architectures.

The network 102 may be implemented as one or more wired networks, wireless networks or some combination of wired and wireless networks. The network may include private, public, academic, business or government networks, or any of a number of different combinations thereof, and in the context of an Internet-based computing architecture, includes the Internet. The network may support one or more of any of a number of different communications protocols, technologies or the like, such as cellular telephone, Wi-Fi, satellite, cable, digital subscriber line (DSL), fiber optics and the like.

The systems and computers connected to the network 102 may also be implemented in a number of different manners. In some examples, the dynamic display 104 is implemented as a smart interactive display device, tablet computer or the like. In some examples, the dynamic display also includes a suitable user input interface such as a touch-sensitive surface that may be separate from or integrated into a touchscreen. As shown, the dynamic display is a network-connected display device, and it may be configured to communicate with another computer such as the information server 106 over the network. In other examples, the dynamic display and information server may be co-located, in which case the dynamic display may or may not be network-connected.

The information server 106 is commonly implemented as a server computer although other implementations are contemplated (e.g., mainframe computer, personal computer). The information server may be embodied as one or more servers, a network of interworking computing devices (e.g., a distributed computer implemented by multiple computers) or the like. In implementations in which the information server is implemented as a distributed computer, its multiple computers may communicate over a network such as network 102.

The mobile device 108 is generally a small, mobile computing device such as a smartphone. Other examples of suitable mobile devices include portable computers (e.g., laptop computers, tablet computers), cellular phones, wearable computers (e.g., smartwatches, optical head-mounted displays) and the like. According to example implementations, the mobile device includes a biometric sensor or multiple biometric sensors (i.e., one or more biometric sensors) configured to acquire physiological markers from which a user is identifiable and thereby authenticated (e.g., fingerprint, palm print, hand geometry, face recognition, iris recognition, retina recognition). The mobile device also includes built-in short-range communication technology and is contactless payment capable. One example of suitable short-range communication technology is near-field communication (NFC). Other examples include radio frequency identification (RFID), personal area network technologies such as Bluetooth, Bluetooth LE, ZigBee, infrared (e.g., Infrared Data Association (IrDA)) and the like.

The POS system 110 is generally a system used by a merchant to effect sales transactions, record sales and track inventory. The POS system includes one or more of each of a number of components including the POS terminal 112 and server 114. The POS terminal is a special-purpose computer that interfaces with payment cards and other payment technologies to make electronic funds transfers. The POS server is configured to transmit data from the POS terminal to a merchant service provider for authorization and transfer of funds to the merchant. Similar to the mobile device 108, the POS terminal includes built-in short-range communication technology and is contactless payment capable.

Similar to the information server 106, the POS server 114, authentication server 116 and authorization server 118 are each commonly implemented as a server computer although other implementations are contemplated (e.g., mainframe computer, personal computer). Any combination or all of the POS server, authentication server and authorization server may be embodied as one or more servers, a network of interworking computing devices (e.g., a distributed computer implemented by multiple computers) or the like. In implementations in which the server is implemented as a distributed computer, its multiple computers may communicate over a network such as network 102. And in some examples, more than one of the servers (e.g., authentication server and authorization server) are co-located.

Figure 2:
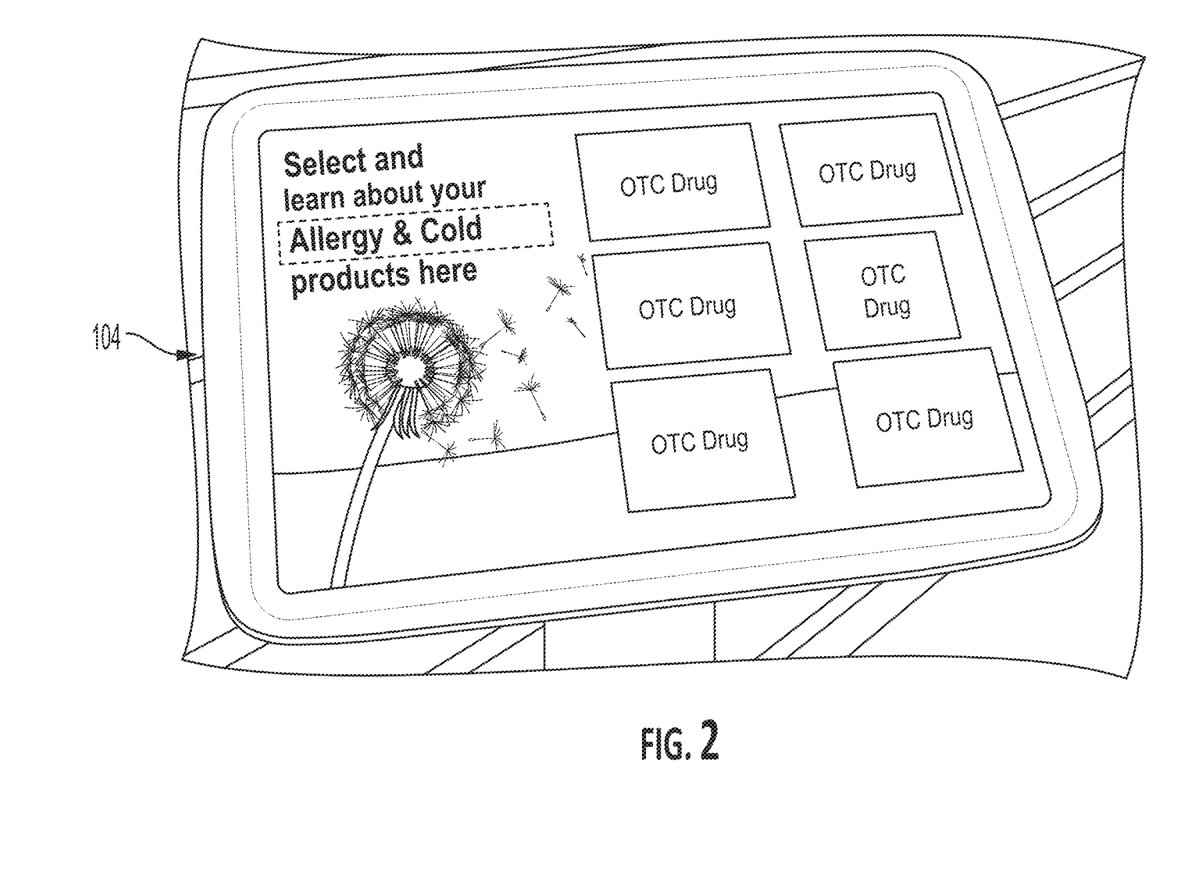
FIG. 2 further illustrates a dynamic display of the system of FIG. 1, according to some example implementations.

Reference is now made to FIG. 2 which further illustrates the dynamic display 104 according to some example implementations. As explained above, merchants of certain OTC drugs such as those regulated by the CMEA restrict public access to those products. A number of merchants advertise these products with other products in a retail shelf environment but with cards that are redeemed for the product at the time of purchase. These product cards are often inconveniently placed and occupy valuable space on shelves. The dynamic display of example implementations offers the same information as product cards and may be free-standing or shelf mounted, and may free the shelf space otherwise occupied by product cards for more physical products and packages.

Figure 3A:
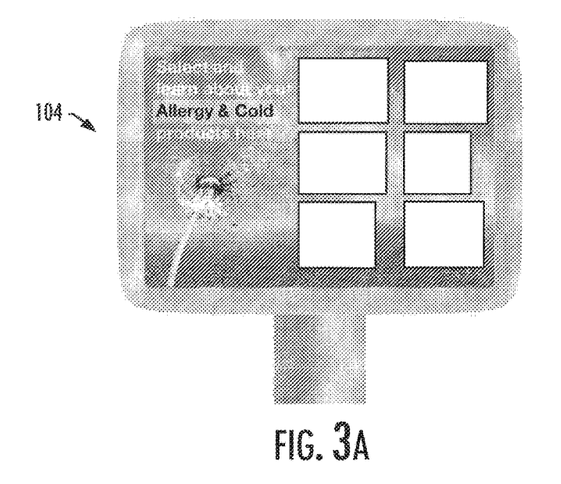
FIGS. 3A, 3B, 3C and 3D illustrate an example interaction with the dynamic display according to some example implementations.

FIGS. 3A, 3B, 3C and 3D illustrate an example interaction with the dynamic display 104 according to some examples in which the dynamic display includes a touchscreen. In the illustrated example, the dynamic display communicates with the information server 106 (co-located or across network 102) to deliver information regarding allergy and cold medicines. In some examples, a user may be led to allergy and cold medicines by first selecting a condition from a plurality of conditions. The dynamic display may then identify a number of brands of allergy and cold medicines. As shown in FIG. 3A, the dynamic display identifies brands of medicines by images of their packaging, but other manners of identifying brands are contemplated.

Figure 3B:
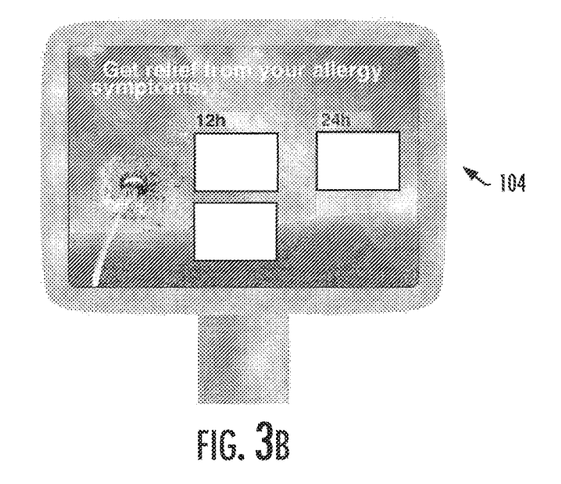

From the display in FIG. 3A, the user selects a brand of medicine which in turn causes the dynamic display 104 to present information regarding the selected brand. In instances in which the brand has a number of varieties, the dynamic display may first identify those varieties for selection. This is shown in FIG. 3B in which the varieties are identified by images of their packaging, although again, other manners of identifying the varieties of a selected brand of medicine are also contemplated.

Figure 3C:
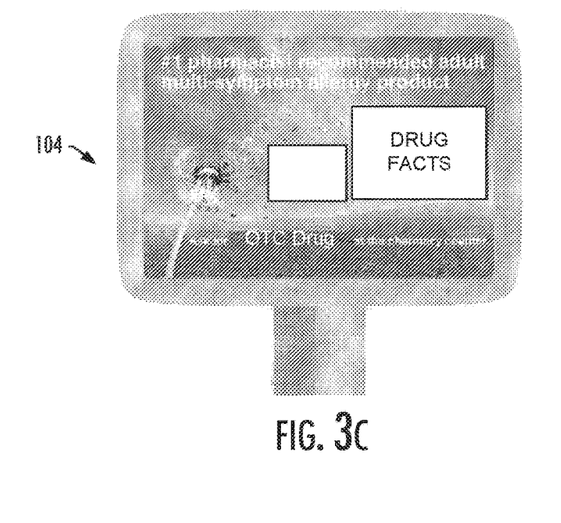
Figure 3D:
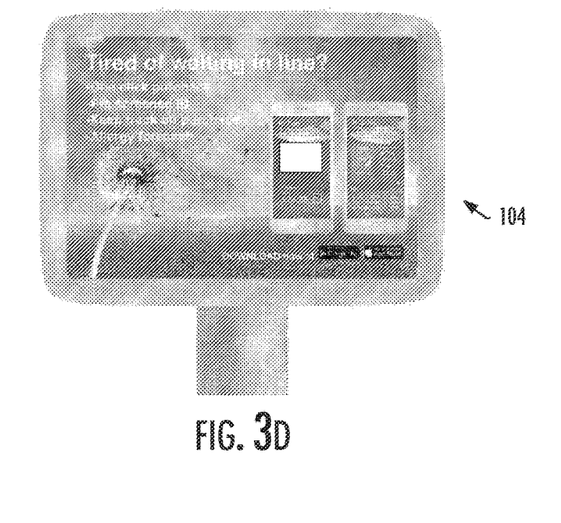

FIG. 3C illustrates the dynamic display 104 presenting information regarding a selected band of medicine, or a selected variety of the selected brand. As shown, this drug-specific information includes the same or similar information to the drug label on the packaging of the selected medicine, although other information may be presented in addition to or in lieu of the drug label. This information serves to inform and educate the user regarding the selected product. The dynamic display also provides purchase instructions, which in some but not all examples includes directing the user as to how to ask the merchant (pharmacist) for the selected medicine. In some examples, the manufacturer of the selected medicine may offer a mobile app that the user can install on their mobile device 108 to expedite purchase of the medicine. In these examples, the dynamic display may present instructions to the user to download the app, as shown in FIG. 3D.

As also explained above, not only does the CMEA requires merchants to restrict public access to regulated products (e.g., PSE), but the CMEA also requires merchants to verify proof of identity of all purchasers, and track all purchasers and purchases. This is time consuming and inconvenient. Some example implementations of the present disclosure include a mobile app for a mobile device 108 that enables biometric authentication for restricted over-the-counter (OTC) drug sales, as well as the secure electronic tracking of those sales. In some examples, the mobile app is provided by a service provider with which a user of the mobile app registers an account, and during this registration, the service provider verifies the user's identity by a valid proof of identity such as a government-issued identification card, driver's license or the like.

Figure 4:
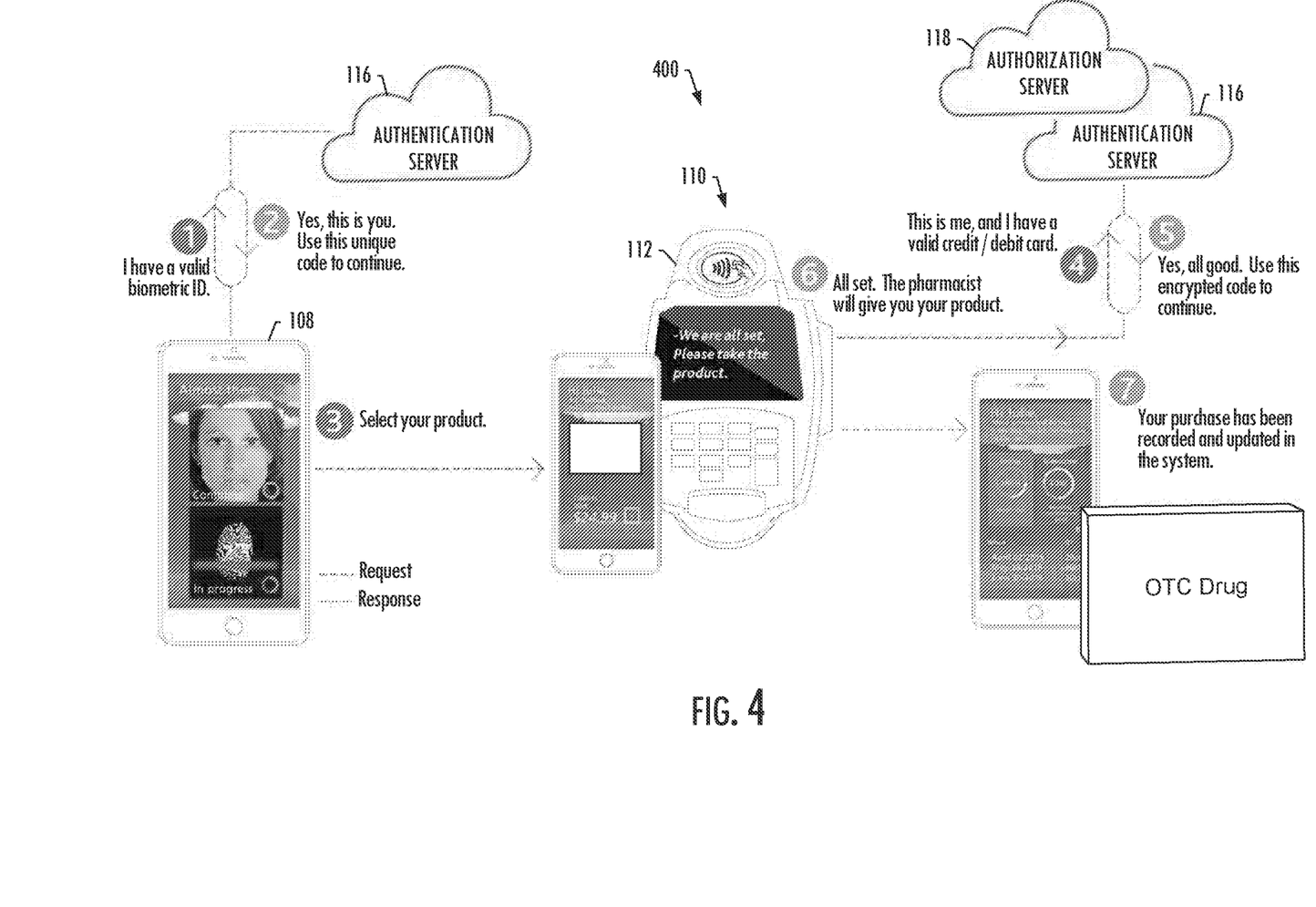
FIGS. 4 and 5 illustrate process flow diagrams according to example implementations.

FIG. 4 illustrates a process flow diagram 400 with various operations performed to carry out a restricted OTC drug sale according to some example implementations of the present disclosure. As shown, the service provider operates the authentication server 116 that implements a mobile app server or other appropriate middleware component for providing back-end functionality to the mobile app installed on a mobile device 108.

As also shown, the mobile app causes one or more biometric sensors on the mobile device 108 to acquire a physiological marker from which a user may be identified and thereby authenticated. This physiological marker may be considered a biometric identifier (ID). The mobile app may identify and thereby authenticate the user based on this biometric ID and data locally on the mobile device, or communicate the biometric ID to the authentication server 116 to perform the identification/authentication. In instances in which the mobile app performs the identification/authentication, the mobile app may instead send a message to the authentication server that indicates the user has been authenticated. In either instance, the authentication server is responsive to an authenticated user with a unique authentication code transmitted back to the mobile app.

The mobile app on the mobile device 108 allows the user to select a desired OTC drug. The mobile device interacts with the POS terminal 112 of the POS system 110 to purchase the selected OTC drug using respective short-range communication and contactless payment capabilities of the devices. This short-range communication between the mobile device and POS terminal may lock-in the biometric ID and the location of the mobile device (the POS terminal's location being known). The mobile app sends a purchase message including the unique authentication code, an identifier of the desired OTC drug, and appropriate payment information. This payment information may include payment (credit, debit) card information, or other appropriate information such as a payment token as may be used in systems such as Apple Pay, Android Pay or Samsung Pay.

In some examples, the purchase message is sent to the authentication server 116 or authorization server 118 which cooperate with one another to enable the authentication server to validate the authentication code, and enable the authorization server to authorize the payment based on the payment information. The authentication server may also at this time electronically record the purchase transaction including the purchaser, OTC drug and date/time of the purchase. The purchaser may be identified by the authentication code or a unique identifier of the user (e.g., biometric ID). The OTC drug may be identified by its identifier, which may be unique to the product or unit of the product such as in the case of a unique serial number.

After the authentication code is validated and the payment authorized, and the purchase transaction recorded, the authentication server 116 or authorization server 118 returns an encrypted code back to the POS system 110 to authorize the merchant to release the OTC drug to the user/purchaser. In some examples, the encrypted code may also be added to packaging of the OTC drug. This may be accomplished in a number of different manners such as by printing on the packaging, printing on another substrate affixed to the packaging, electronically reading to electronic media (e.g., RFID) on the packaging, or the like.

Figure 5:
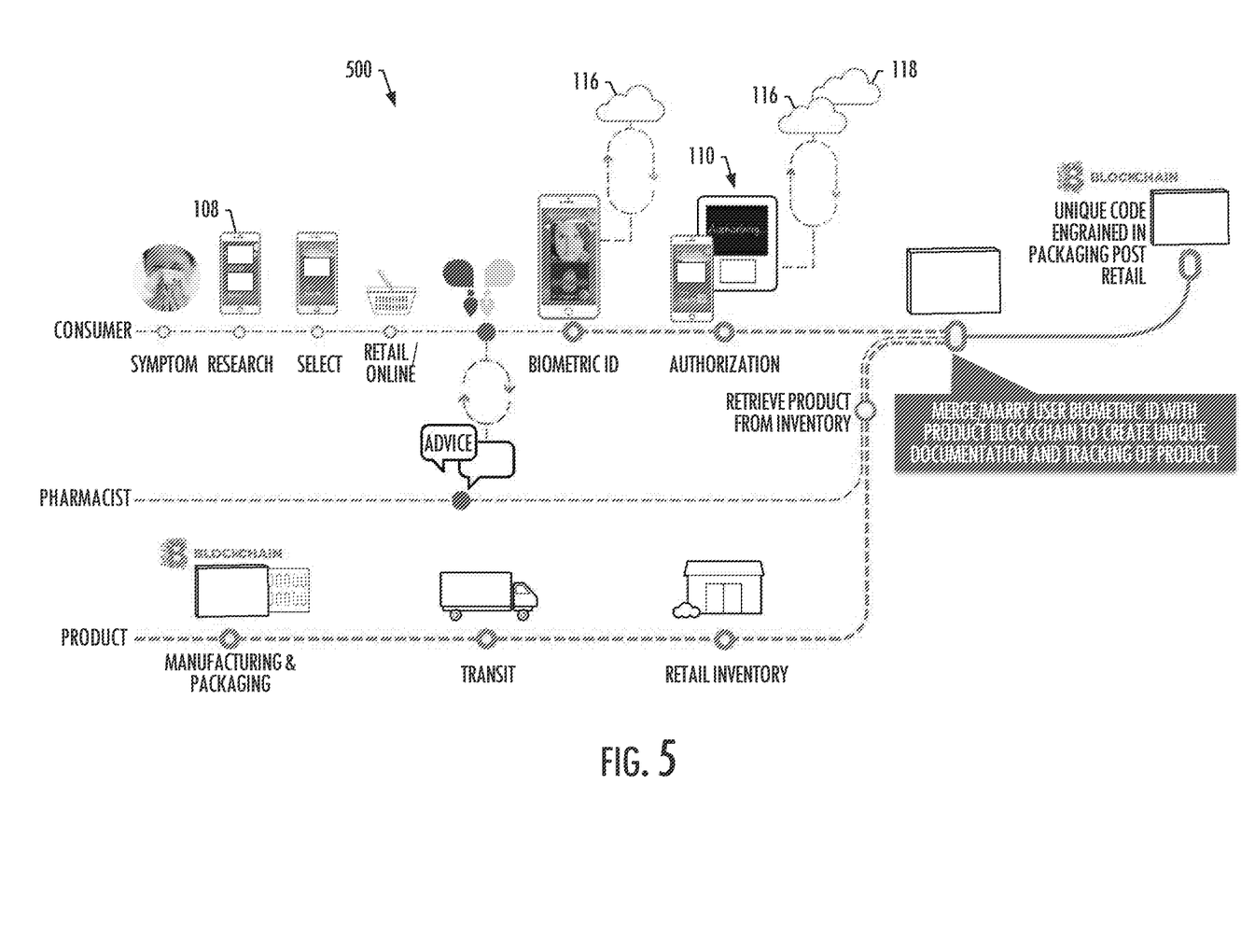

As described above, one or more of the servers 106, 114, 116, 118 of the system 100 may be embodied as a network of interworking computing devices. In some examples, the servers may be embodied as or otherwise form part of network of interworking computing devices, such as in a peer-to-peer computing architecture. This may enable a number of configurations of the system or in which the system participates. One example of a suitable configuration is a distributed database that maintains the record of purchase transactions. And one example of a suitable distributed database is a blockchain, which is a shared, immutable ledger for recording the history of transactions. FIG. 5 is a process flow diagram 500 for a restricted OTC drug sale that expands on the diagram 400 in FIG. 4, and includes a blockchain to record purchase transactions.

As shown in FIG. 5, each OTC drug may be associated with a unique identifier for the unit of product (e.g., serial number), which may be recorded on the blockchain during manufacturing/packaging. The product may be purchased according to the process described above with reference to FIG. 4. During this process, the product blockchain may be used as its identifier. The product blockchain may be merged with the authentication code or user identifier (e.g., biometric ID) and recorded on the blockchain with the date/time of the purchase. In some examples, the data may be encrypted and serve as the aforementioned encrypted code, which may also be added to packaging of the OTC drug. The blockchain may then be used as a secure electronic record of the purchase.

Figure 6:
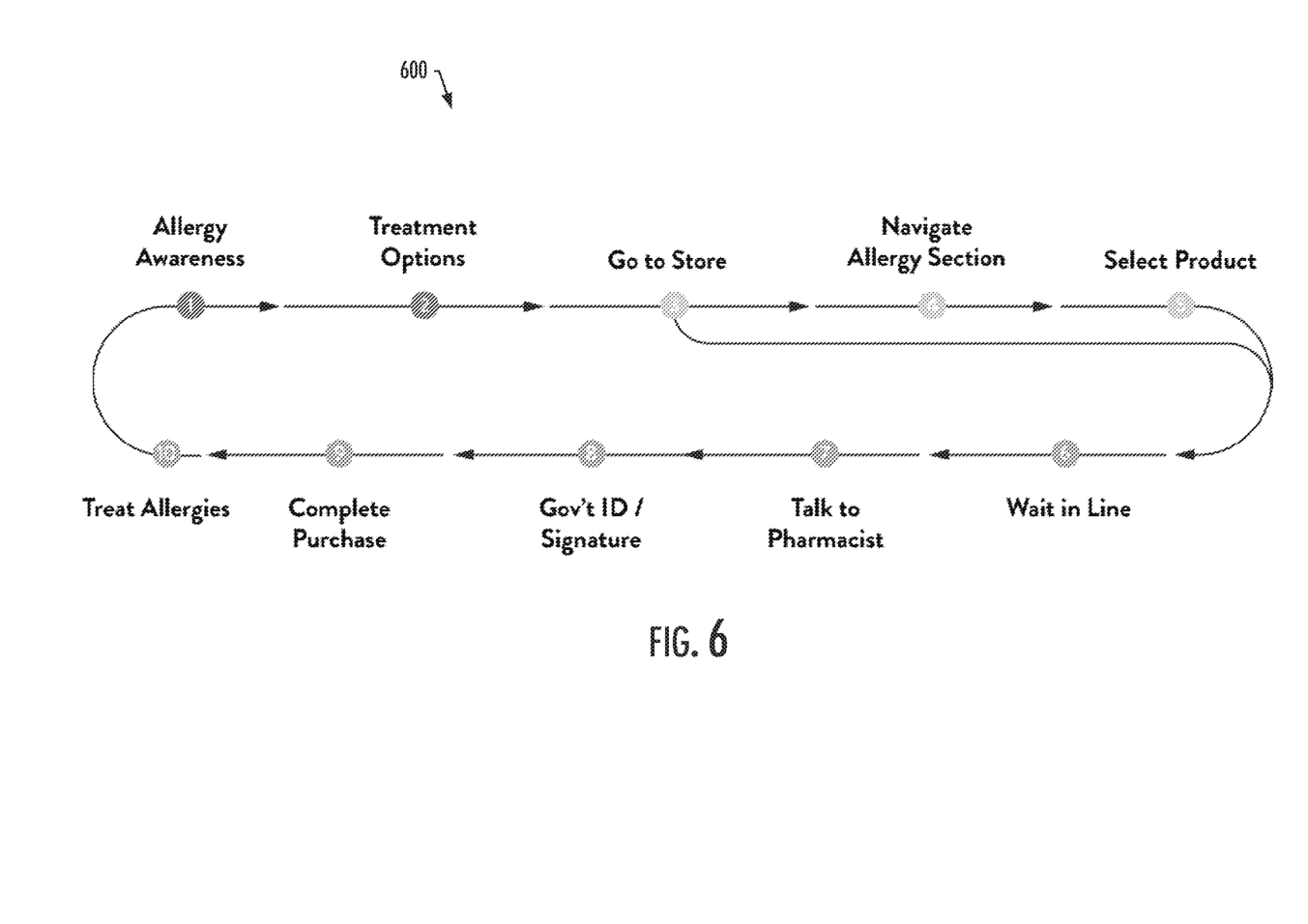
FIGS. 6, 7, 8 and 9 illustrate also process flow diagrams according to example implementations.
Figure 7:
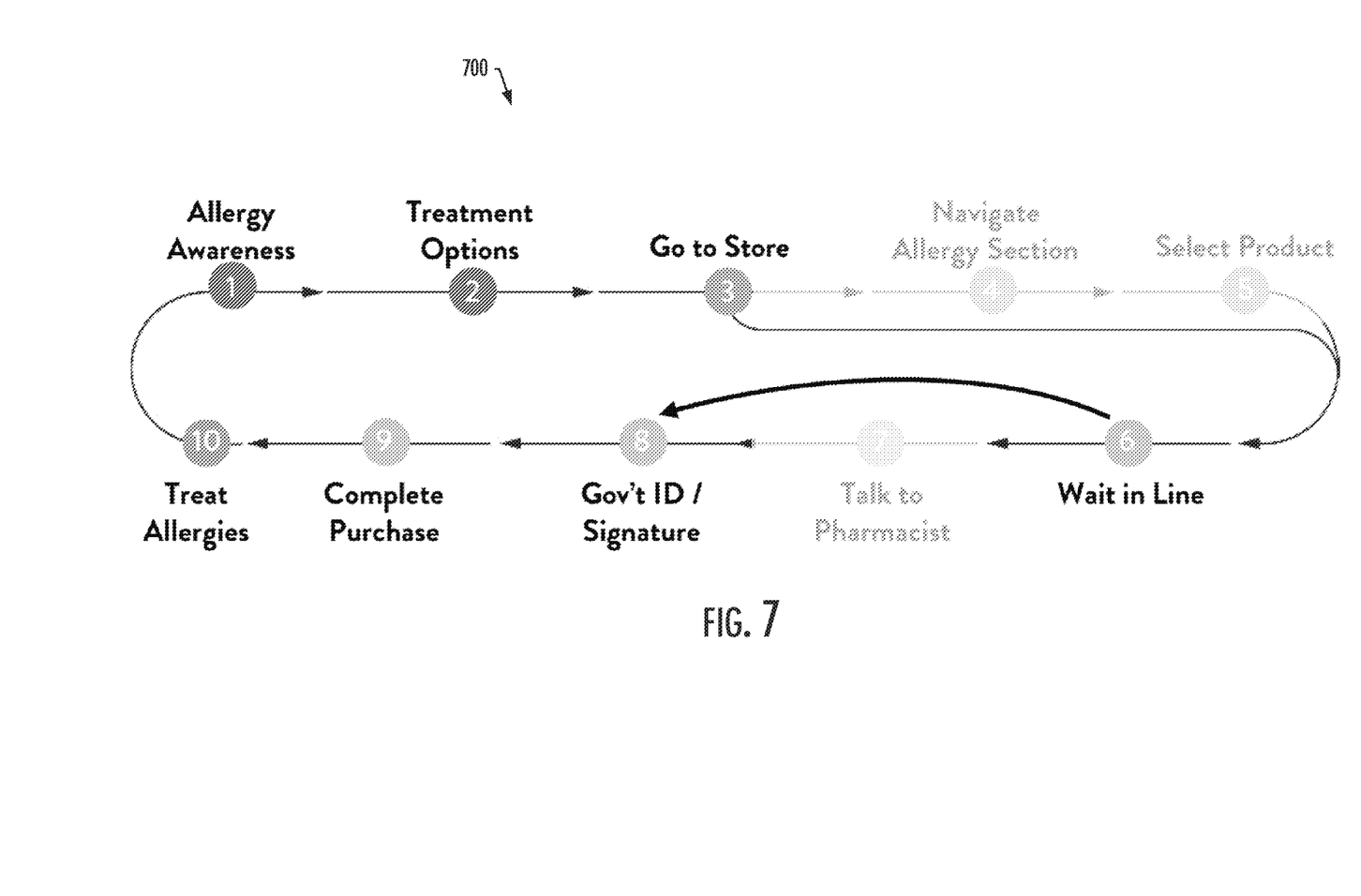

To further illustrate example implementations of the present disclosure, FIG. 6 is a process flow diagram 600 of a typical sale of an allergy medicine that may be streamlined according to example implementations. FIG. 7 illustrates a process flow diagram 700 similar to be streamlined relative to the diagram 600 in FIG. 6 according to some examples. As shown in FIG. 7, after the user (consumer) understands their allergies and treatment needs and options, the user visits the pharmacy where a dynamic display 104 on an aisle with other medicines amplifies information and helps the user find their product and answer questions. In some examples, the dynamic display or a mobile app on the user's mobile device 108 allows the user to choose a medicine and order ahead to the pharmacy for a quicker pickup. In the case of the mobile app, the order may be placed without the user first visiting the pharmacy and interacting with the dynamic display.

Figure 8:
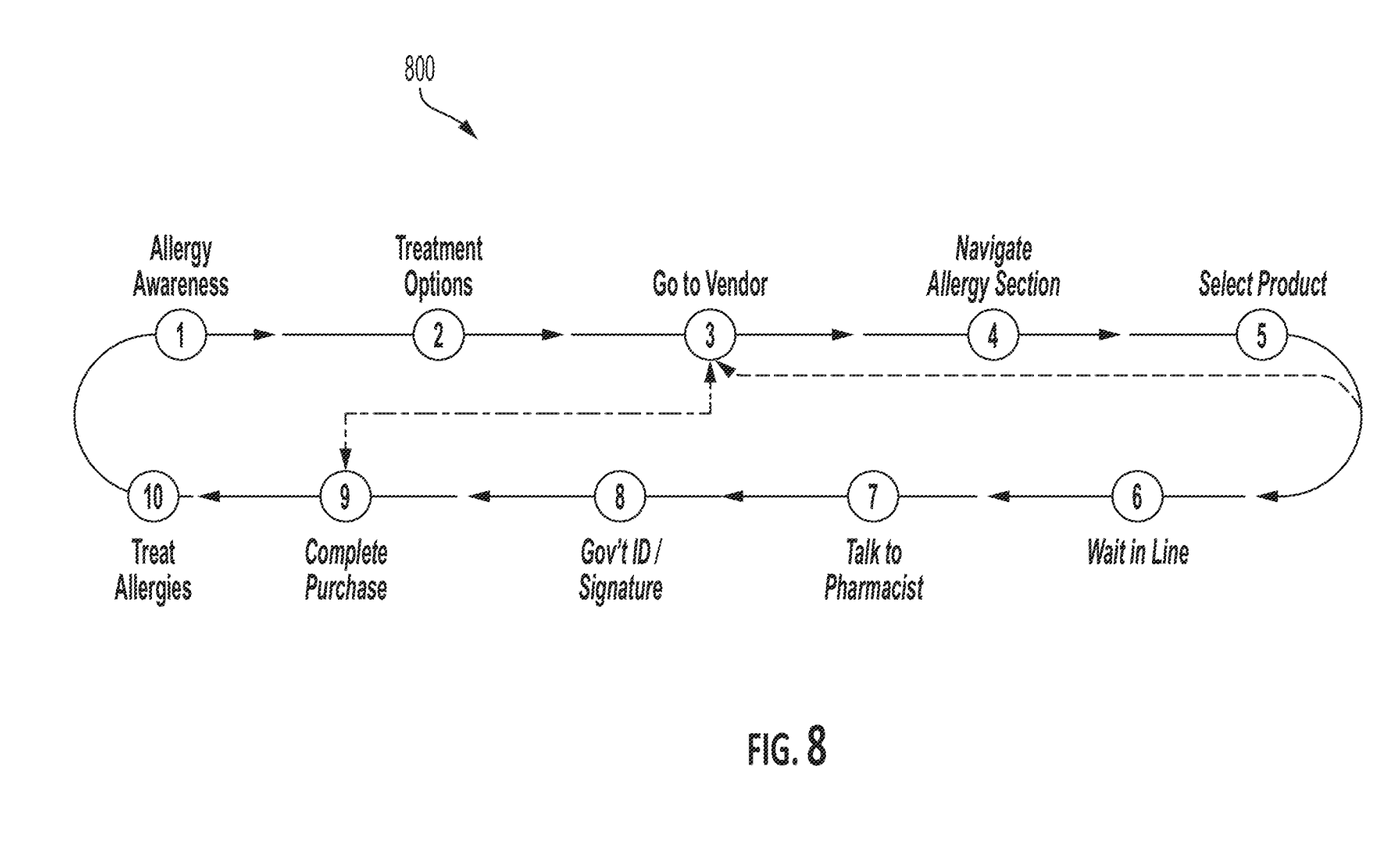

FIG. 8 illustrates another process flow diagram 800 similar to be streamlined relative to the diagram 600 in FIG. 6 according to some examples. As shown in FIG. 8, the dynamic display is implemented by a self-service kiosk or integrated shelf dispenser that combines functionality of the dynamic display 104 and mobile device 108. In some examples, the kiosk/shelf dispenser allows the user to find a product and answer questions, and includes biometric sensors for biometric authentication, and perhaps also a scanner to scan a valid proof of identity. The kiosk/shelf dispenser may then complete the purchase (implementing aspects of the POS system 110) and dispense the medicine. In some examples, the user's mobile device includes a mobile app to enable the user to place an order dispensed by the kiosk/shelf dispenser.

Figure 9:
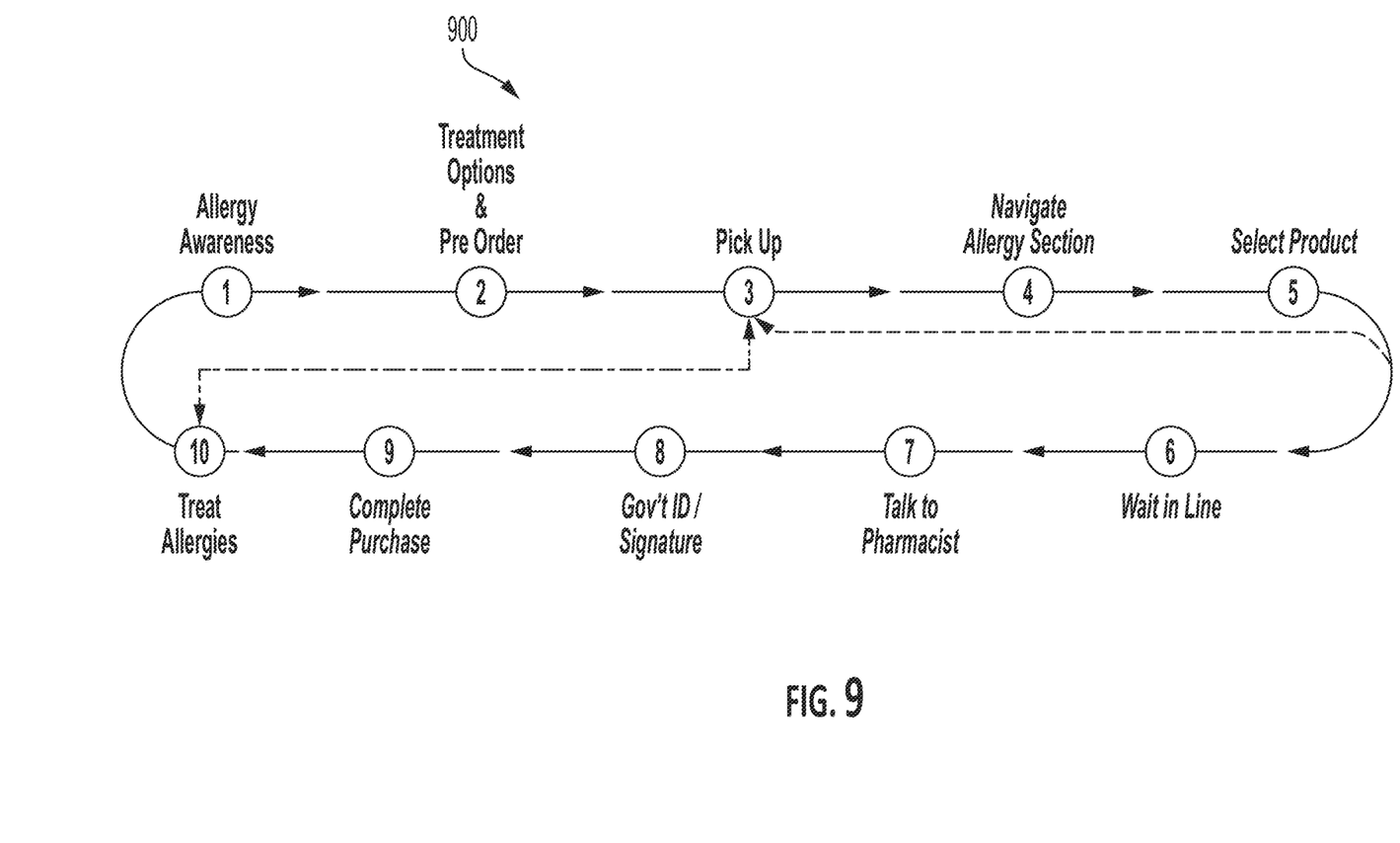

FIG. 9 illustrates yet another process flow diagram 900 similar to be streamlined relative to the diagram 600 in FIG. 6 according to some examples. As shown in FIG. 9, the user goes through an initial onboarding process with the pharmacist or other service provider, similar to described above for registering an account with the service provider providing the mobile app. The user can then use their mobile app to request medicines for pickup at the pharmacist. In some examples, the mobile device 108 performs biometric authentication, as described above. Additionally or alternatively, in some examples, a separate device at the pharmacy includes biometric sensors for biometric authentication, and perhaps also a scanner to scan a valid proof of identity.

According to example implementations of the present disclosure, the system 100 and its subsystems including the dynamic display 104, information server 106, mobile device 108, POS terminal 112, POS server 114, authentication server 116 and authorization server 118 may be implemented by various means. Means for implementing the system and its subsystems may include hardware, alone or under direction of one or more computer programs from a computer-readable storage medium. In some examples, one or more apparatuses may be configured to function as or otherwise implement the system and its subsystems shown and described herein. In examples involving more than one apparatus, the respective apparatuses may be connected to or otherwise in communication with one another in a number of different manners, such as directly or indirectly via a wired or wireless network or the like.

Figure 10:
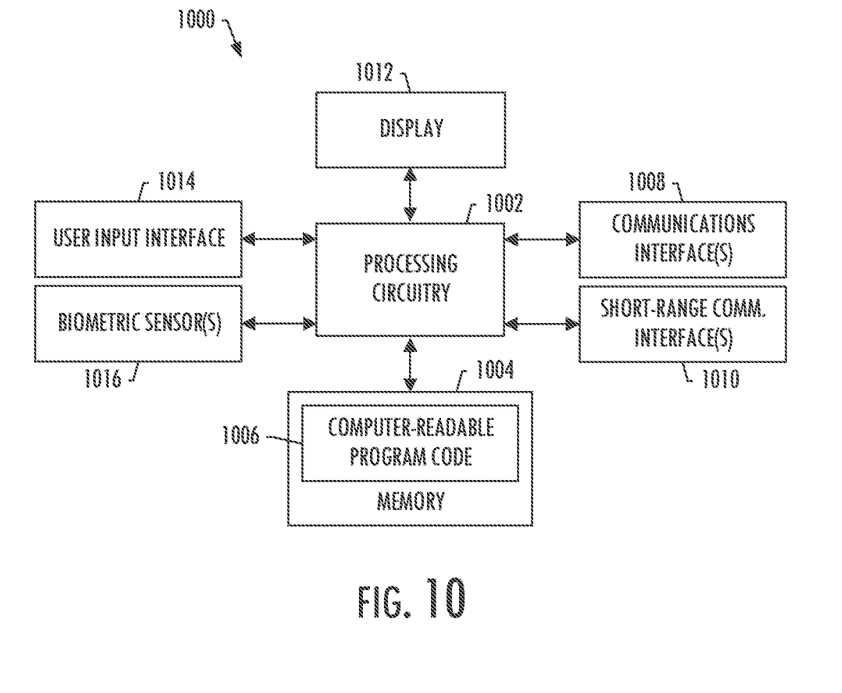
FIG. 10 illustrates an apparatus according to example implementations.

FIG. 10 illustrates an apparatus 1000 according to some example implementations of the present disclosure. Generally, an apparatus of exemplary implementations of the present disclosure may comprise, include or be embodied in one or more fixed or portable electronic devices. The apparatus may include one or more of each of a number of components such as, for example, a processor 1002 connected to a memory 1004 (e.g., storage device).

The processor 1002 may be composed of one or more processors alone or in combination with one or more memories. The processor is generally any piece of computer hardware that is capable of processing information such as, for example, data, computer programs and/or other suitable electronic information. The processor is composed of a collection of electronic circuits some of which may be packaged as an integrated circuit or multiple interconnected integrated circuits (an integrated circuit at times more commonly referred to as a "chip"). The processor may be configured to execute computer programs, which may be stored onboard the processor or otherwise stored in the memory 1004 (of the same or another apparatus).

The processor 1002 may be a number of processors, a multi-core processor or some other type of processor, depending on the particular implementation. Further, the processor may be implemented using a number of heterogeneous processor systems in which a main processor is present with one or more secondary processors on a single chip. As another illustrative example, the processor may be a symmetric multi-processor system containing multiple processors of the same type. In yet another example, the processor may be embodied as or otherwise include one or more ASICs, FPGAs or the like. Thus, although the processor may be capable of executing a computer program to perform one or more functions, the processor of various examples may be capable of performing one or more functions without the aid of a computer program. In either instance, the processor may be appropriately programmed to perform functions or operations according to example implementations of the present disclosure.

The memory 1004 is generally any piece of computer hardware that is capable of storing information such as, for example, data, computer programs (e.g., computer-readable program code 1006) and/or other suitable information either on a temporary basis and/or a permanent basis. The memory may include volatile and/or non-volatile memory, and may be fixed or removable. Examples of suitable memory include random access memory (RAM), read-only memory (ROM), a hard drive, a flash memory, a thumb drive, a removable computer diskette, an optical disk, a magnetic tape or some combination of the above. Optical disks may include compact disk-read only memory (CD-ROM), compact disk-read/write (CD-R/W), DVD or the like. In various instances, the memory may be referred to as a computer-readable storage medium. The computer-readable storage medium is a non-transitory device capable of storing information, and is distinguishable from computer-readable transmission media such as electronic transitory signals capable of carrying information from one location to another. Computer-readable medium as described herein may generally refer to a computer-readable storage medium or computer-readable transmission medium.

In addition to the memory 1004, the processor 1002 may also be connected to one or more interfaces for displaying, transmitting and/or receiving information. The interfaces may include one or more communications interfaces and/or one or more user interfaces. The communications interface(s) may be configured to transmit and/or receive information, such as to and/or from other apparatus(es), network(s) or the like. The communications interface may be configured to transmit and/or receive information by physical (wired) and/or wireless communications links. The communications interface(s) may include interface(s) 1008 to connect to a network (e.g., network 102), such as using technologies such as cellular telephone, Wi-Fi, satellite, cable, digital subscriber line (DSL), fiber optics and the like. And at least in instances in which the apparatus 1000 is configured to implement the mobile device 108 or POS terminal 112, the communications interface(s) may include one or more short-range communications interfaces 1010 configured to connect devices using short-range communications technologies such as NFC, RFID, Bluetooth, Bluetooth LE, ZigBee, infrared (e.g., IrDA) or the like.

The user interfaces may include a display 1012 and/or one or more user input interfaces 1014. The display may be configured to present or otherwise display information to a user, suitable examples of which include a liquid crystal display (LCD), light-emitting diode display (LED), plasma display panel (PDP) or the like. The user input interfaces may be wired or wireless, and may be configured to receive information from a user into the apparatus, such as for processing, storage and/or display. Suitable examples of user input interfaces include a microphone, image or video capture device, keyboard or keypad, joystick, touch-sensitive surface (separate from or integrated into a touchscreen) or the like. In instances in which the apparatus 1000 is configured to implement the mobile device 108, the user interfaces may include one or more biometric sensors 1016 such as cameras or scanners capable of acquiring markers for or enabling technology such as fingerprint, palm print, hand geometry, face recognition, iris recognition, retina recognition. The user interfaces may further include one or more interfaces for communicating with peripherals such as printers, scanners or the like.

As indicated above, program code instructions may be stored in memory, and executed by processor that is thereby programmed, to implement functions of the systems, subsystems, tools and their respective elements described herein. As will be appreciated, any suitable program code instructions may be loaded onto a computer or other programmable apparatus from a computer-readable storage medium to produce a particular machine, such that the particular machine becomes a means for implementing the functions specified herein. These program code instructions may also be stored in a computer-readable storage medium that can direct a computer, processor or other programmable apparatus to function in a particular manner to thereby generate a particular machine or particular article of manufacture. The instructions stored in the computer-readable storage medium may produce an article of manufacture, where the article of manufacture becomes a means for implementing functions described herein. The program code instructions may be retrieved from a computer-readable storage medium and loaded into a computer, processor or other programmable apparatus to configure the computer, processor or other programmable apparatus to execute operations to be performed on or by the computer, processor or other programmable apparatus.

Retrieval, loading and execution of the program code instructions may be performed sequentially such that one instruction is retrieved, loaded and executed at a time. In some example implementations, retrieval, loading and/or execution may be performed in parallel such that multiple instructions are retrieved, loaded, and/or executed together. Execution of the program code instructions may produce a computer-implemented process such that the instructions executed by the computer, processor or other programmable apparatus provide operations for implementing functions described herein.

Execution of instructions by processor, or storage of instructions in a computer-readable storage medium, supports combinations of operations for performing the specified functions. In this manner, an apparatus 1000 may include processor 1002 and a computer-readable storage medium or memory 1004 coupled to the processor, where the processor is configured to execute computer-readable program code 1006 stored in the memory. It will also be understood that one or more functions, and combinations of functions, may be implemented by special purpose hardware-based computer systems and/or processor which perform the specified functions, or combinations of special purpose hardware and program code instructions.

As explained above, the present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as combinable, unless the context of the disclosure clearly dictates otherwise.

Many modifications and other implementations of the disclosure set forth herein will come to mind to one skilled in the art to which the disclosure pertains having the benefit of the teachings presented in the foregoing description and the associated drawings. Therefore, it is to be understood that the disclosure is not to be limited to the specific implementations disclosed and that modifications and other implementations are intended to be included within the scope of the appended claims. Moreover, although the foregoing description and the associated drawings describe example implementations in the context of certain example combinations of elements and/or functions, it should be appreciated that different combinations of elements and/or functions may be provided by alternative implementations without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A mobile device comprising:
   one or more biometric sensors configured to acquire a physiological marker from which a user is identifiable and thereby authenticated;
   a short-range communication interface configured to implement short-range communication technology and enable contactless payment capability of the mobile device; and
   a processor coupled to the one or more biometric sensors and short-range communication interface, and programmed to at least:
   cause the one or more biometric sensors to acquire the physiological marker, and identify and authenticate the user based thereon;
   send a message to an authentication server that indicates the user is authenticated, and receive a response from the authentication server that includes a unique authentication code;
   receive selection of a thereby selected over-the-counter (OTC) drug; and
   communicate with a point-of-sale (POS) system with contactless payment capability, to purchase the selected OTC drug using the short-range communication interface and the contactless payment capabilities of the mobile device and POS system,
   wherein the processor being programmed to communicate with the POS system includes being programmed to send a purchase message to the POS system that includes the unique authentication code an identifier of the selected OTC drug, and payment information, the POS system being configured to communicate with the authentication server to validate the unique authentication code and to record a purchase transaction on a blockchain and with an authorization server to authorize payment for the selected OTC drug based on the payment information,
   wherein the authentication server is operated by a service provider, and the processor is further programmed to enable the user to register an account with the service provider before the message is sent to the authentication server, and the processor is programmed to enable the service provider to verify the identity of the user during account registration, and
   wherein the identifier of the selected OTC drug is unique to a unit thereof, the identifier of the selected OTC drug is recorded on the blockchain during manufacturing or packaging, and the purchase transaction recorded on the blockchain includes an identifier for the user, the identifier of the selected OTC drug, and a date and/or a time of purchase.

2. The mobile device of claim 1, wherein the POS system has a known location, and the processor being programmed to authenticate the user based on the physiological marker and communicate with the POS system using the short-range communication interface locks-in the user thereby authenticated at the known location.

3. The mobile device of claim 1, wherein the processor is further programmed to at least:
   capture data from a proof of identity of the user; and
   send the data to the service provider to enable the service provider to verify the identity of the user from the data, the identity of the user being verified before the authentication server is enabled to send the response that indicates the unique authentication code.

4. An apparatus configured to implement a self-service kiosk or integrated shelf dispenser, the apparatus comprising:
   one or more biometric sensors configured to acquire a physiological marker from which a user is identifiable and thereby authenticated;
   a processor coupled to the one or more biometric sensors, and programmed to at least:
   cause the one or more biometric sensors to acquire the physiological marker, and identify and authenticate the user based thereon;
   send a message to an authentication server that indicates the user is authenticated, and receive a response from the authentication server that includes a unique authentication code;
   receive selection of a thereby selected over-the-counter (OTC) drug;
   complete a purchase of the selected OTC drug, including the processor being programmed to send a purchase message to the authentication server that includes the unique authentication code, an identifier of the selected OTC drug, and payment information, the processor being programed to send the purchase message for the authentication server to validate the unique authentication code and to record the purchase transaction on a blockchain and for the authentication server to cooperate with an authorization server to authorize payment for the selected OTC drug based on the payment information; and
   receive an encrypted code to authorize release of the selected OTC drug,
   wherein the authentication server is operated by a service provider, and the processor is further programmed to enable the user to register an account with the service provider before the message is sent to the authentication server, and the processor is programmed to enable the service provider to verify the identity of the user during account registration, and
   wherein the identifier of the selected OTC drug is unique to a unit thereof, the identifier of the selected OTC drug is recorded on the blockchain during manufacturing or packaging, and the purchase transaction recorded on the blockchain includes an identifier for the user, the identifier of the selected OTC drug, and a date and/or a time of purchase; and a dispenser coupled to the processor and caused thereby to dispense the selected OTC drug after the purchase is completed.

5. The apparatus of claim 4, wherein the processor is further programmed to at least:

capture data from a proof of identity of the user; and send the data to the service provider to enable the service provider to verify the identity of the user from the data, the identity of the user being verified before the authentication server is enabled to send the response that indicates the unique authentication code.

6. An apparatus configured to implement an authentication server, the apparatus comprising:

a processor and a memory storing executable instructions that in response to execution by the processor cause the apparatus to at least:

receive a message related to a purchase of an over-the-counter (OTC) drug by a user, the message indicating the user is authenticated, the message being received from a mobile device, self-service kiosk or integrated shelf dispenser;

send a response to the mobile device, self-service kiosk or integrated shelf dispenser, the response including a unique authentication code;

receive a purchase message that includes the unique authentication code, an identifier of a selected OTC drug, and payment information, the purchase message being received from a point-of-sale (POS) system, or the self-service kiosk or integrated shelf dispenser;

validate the unique authentication code;

record a purchase transaction on a blockchain;

cooperate with an authorization server to authorize payment for the selected OTC drug based on the payment information; and return an encrypted code to the POS system, self-service kiosk or integrated shelf dispenser to authorize release of the selected OTC drug, wherein the apparatus is operated by a service provider, and the processor is further programmed to enable the user to register an account with the service provider before the message related to the purchase of the OTC drug is received by the apparatus, and the processor is programmed to enable the service provider to verify the identity of the user during account registration, and wherein the identifier of the selected OTC drug is unique to a unit thereof, the identifier of the selected OTC drug is recorded on the blockchain during manufacturing or packaging, and the purchase transaction recorded on the blockchain includes an unique for the user, the identifier of the selected OTC drug, and the date and/or time of purchase.

7. A method comprising:

acquiring, via one or more biometric sensors of a mobile device, a physiological marker from which a user is identifiable and thereby authenticated; and at the mobile device;

identifying and authenticating the user based on the physiological marker;

sending a message to an authentication server that indicates the user is authenticated, and receiving a response from the authentication server that includes a unique authentication code;

receiving selection of a thereby selected over-the-counter (OTC) drug; and communicating with a point-of-sale (POS) system with contactless payment capability, to purchase the selected OTC drug using the short-range communication interface and the contactless payment capabilities of the mobile device and POS system, wherein communicating with the POS system includes sending a purchase message to the POS system that includes the unique authentication code, an identifier of the selected OTC drug, and payment information, the POS system communicating with the authentication server to validate the unique authentication code and to record a purchase transaction on a blockchain and with an authorization server to authorize payment for the selected OTC drug based on the payment information, wherein the authentication server is operated by a service provider, and the user registers an account with the service provider before the message is sent to the authentication server, and the service provider verifies the identity of the user during account registration, and wherein the identifier of the selected OTC drug is unique to a unit thereof, the identifier of the selected OTC drug is recorded on the blockchain during manufacturing or packaging, and the purchase transaction recorded on the blockchain includes the unique identifier for the user, the identifier of the selected OTC drug, and a date and/or a time of purchase.

8. The method of claim 7, wherein the POS system has a known location, and authenticating the user based on the physiological marker and communicating with the POS system using the short-range communication interface locks-in the user thereby authenticated at the known location.

9. The method of claim 7, further comprising:

capturing data from a proof of identity of the user; and sending the data to the service provider to enable the service provider to verify the identity of the user from the data, the identity of the user being verified before the authentication server is enabled to send the response that indicates the unique authentication code.

* * * * *